United States Patent [19]

Schubert et al.

[11] Patent Number: 5,153,333

[45] Date of Patent: Oct. 6, 1992

[54] PRODUCTION OF CYCLIC CARBONATES

[75] Inventors: Frank Schubert, Neukirchen-Vluyn; Rolf Herzog, Bottrop; Bert Meier, Menden; Jürgen Zehrfeld, Voerde, all of Fed. Rep. of Germany

[73] Assignee: Rutgerswerke AG, Fed. Rep. of Germany

[21] Appl. No.: 761,236

[22] Filed: Sep. 17, 1991

[30] Foreign Application Priority Data

Sep. 25, 1990 [DE] Fed. Rep. of Germany ....... 4030283

[51] Int. Cl.$^5$ ........................................... C07D 317/12
[52] U.S. Cl. .................... 549/230; 549/228; 549/229
[58] Field of Search ..................... 549/228, 229, 230

[56] References Cited

U.S. PATENT DOCUMENTS

| | | | |
|---|---|---|---|
| 4,786,741 | 11/1988 | Sachs | 549/230 |
| 4,851,555 | 7/1989 | Weinstein | 549/230 |
| 4,892,954 | 1/1990 | Brindopke et al. | 549/229 |
| 4,931,571 | 6/1990 | Weinstein | 549/230 |

FOREIGN PATENT DOCUMENTS

| | | | |
|---|---|---|---|
| 300794 | 1/1989 | European Pat. Off. | 549/230 |
| 27223 | 7/1972 | Japan | 549/230 |
| 9013776 | 1/1984 | Japan | 549/229 |

*Primary Examiner*—Cecilia Tsang
*Attorney, Agent, or Firm*—Bierman and Muserlian

[57] ABSTRACT

A process for the preparation of 2-oxo-1, 3-dioxolanes comprises reacting an epoxy compound having at least one functional epoxy group in the optional presence of an inert solvent with carbon dioxide at 60° C. to 200° C. at normal pressure in the presence of a quaternary phosphonium compound as catalyst and novel quaternary phosphonium compounds useful as catalysts in the said process.

7 Claims, No Drawings

PRODUCTION OF CYCLIC CARBONATES

STATE OF THE ART

Urethane resins which conventionally are produced by conversion of isocyanate compounds have reached a special significance due to their versatile properties as modern materials. Application fields are primarily the lacquer (varnish) and coating sector, adhesive material sector, casting resin application and composite material sector, but their utility is limited by the toxicity of the isocyanates.

Different methods for the production of 2-oxo-1,3-dioxolanes, also called cyclic carbonates, are described in the literature. In WO 84/03701, epoxides dissolved in alcohol such as propylene oxide dissolved in methanol are converted with carbon dioxide to cyclic carbonates in the presence of triphenylphosphine as catalyst at approximately 130° C. and an excess pressure of 21 bars.

Coordinatively unsaturated nickel(0) phosphine complexes are used in U.S. Pat. No. 3,748,345 as suitable catayts for the conversion of epoxy compounds with carbon dioxide. For example, by this process, ethylene oxide is converted to ethylene carbonate in benzolic solution in the presence of Ni(PPh$_3$)$_2$ at 100° C. and 35 bars over a period of 12 hours at 50% with 95% selectivity. Also described in this patent is the conversion of 2-butylene oxide and epichlorohydrin.

EP Application No. 212,409 carries out the reaction at normal or slightly elevated pressure using catalysts such as quaternary ammonium compounds, amines, phosphines, guanidines and amidines. The process also requires co-catalysts to obtain a sufficient reaction rate which may be alkali metal or alkaline earth metal halides or carbonates.

Examples of suitable catalysts for this process are triethylammonium bromide, benzyl trimethyl ammonium carbonate, triphenylphosphine, piperazine, tetramethyl guanidine and imidazole and preferred co-catalysts are potassium iodide and sodium iodide. The reaction can take place directly or in solution in a solvent such as xylene, toluene, tetrahydrofuran, dimethylsulfoxide and diethyleneglycol methyl ether.

A typical example is the conversion of glycidyl ether "Beckopox E 140" with carbon dioxide at normal pressure and 120° C. in the presence of triphenylphosphine and potassium iodide. In a reaction time of 18 hours, 2-oxo-1,3-dioxolane is produced with a yield of 97.9% and 0.3% residual epoxy content and the reaction time fluctuates between 12 and 29 hours depending on the effectiveness of the catalyst system.

Known are further processes which are carried out in the presence of the following catalysts: active carbon treated with alkali metals, metal halides such as for example magnesium or calcium halides, amines, quaternary ammonium compounds, ammonium halides, organic sulfonic acid salts, phosphonium compounds, hydrazines or guanidines. All processes known until now have, however, a number of disadvantages such as low reaction rates so that increased temperatures and pressures must be used, low yields, products contaminated by side reactions and catalyst residues, and, when using hydrazines, toxicity and the danger of explosion. Even the process of publication EP-A 212,409 which can be carried out at normal pressure in good yields and selectivities requires long reaction times. Catalysts and co-catalysts used must be removed in expensive ways through filtering or recrystallization to obtain good product qualities and bright color.

OBJECTS OF THE INVENTION

It is an object of the invention to provide synthetic resins containing urethane groups free of toxic substances such as free isocyanates or phosgenes used as intermediates.

It is another object of the invention to provide novel quaternary phosphonium compounds useful as catalysts in said process.

These and other objects and advantages of the invention will become obvious from the following detailed description.

THE INVENTION

The novel process of the invention for the preparation of 2-oxo-1,3-dioxolanes comprises reacting an epoxy compound having at least one functional epoxy group in the optional presence of an inert solvent with carbon dioxide at 60° C. to 200° C. at normal pressure in the presence of a quaternary phosphonium compound as catalyst. In contrast to the prior art processes, the process of the invention can be carried out at normal or slightly greater pressure with short reaction times to obtain a bright product of high quality without further purification.

The novel quaternary phosphonium compounds of the invention are soluble in the reaction product and can remain there without discoloration or any reduction in the quality of the product. The reaction time is surprisingly short and the selectivity is surprisingly high.

The novel quaternary phosphonium compounds of the invention have the formula $$[R_1R_2R_3R_4)P]^+X^- \qquad I$$

wherein $R_1$, $R_2$, $R_3$ and $R_4$ are individually selected from the group consisting of alkyl of 1 to 4 carbon atoms and optionally substituted monocyclic aryl and aralkyl and X is an anion.

Examples of alkyl of 1 to 4 carbon atoms are methyl, ethyl, n-propyl, isopropyl, n-butyl, isobutyl, 2-methyl-3-propyl and 3-methyl-3-propyl. Examples of aryl and aralkyl are phenyl and benzyl which may be optionally substituted with alkyl of 1 to 4 carbon atoms, for example. Examples of X are chlorine, bromine or iodine but anions of other acids may also be used.

Examples of specific compounds of formula I are ethyltriphenyl phosphonium bromide, tetrabutyl phosphonium bromide, tetraphenyl phosphonium chloride, butyltriphenyl phosphonium chloride, 4-ethoxybenzyltriphenyl phosphonium bromide and methoxymethyltriphenyl phosphonium chloride. These compounds can be produced by processes described in Muller, Methoden der organischen Chemie, Vol. XII/1, 4th edition 1963, pp. 79., G. Thieme Verlag Stuttgart.

In the process of the invention, the quaternary phosphonium compounds of formula I are preferably used in amounts of 0.05 to 10%, more preferably 0.1 to 5.0%, by weight based on the epoxy compound. The reaction of the epoxy compound and carbon dioxide can take place in the presence or absence of an inert organic solvent.

If the viscosity of the epoxy compound or the resulting 2-oxo-1,3-dioxolane is low at the reaction temperature, no solvent is usually used. If the reaction mixture occurs as a viscous melt at the reaction temperature or if further processing in solution is desired, an inert organic solvent is used. Examples of such solvents are toluene, xylene, tetrahydrofuran, dimethylsulfoxide or monomethyl ether of diethyleneglycol. If a solvent is used, the epoxy compound is preferably dissolved in the solvent at 0.5 to 5 fold of its volume and then reacted with carbon dioxide in the presence of the catalyst.

All epoxy compounds which contain at least one epoxy group can be used in the process. Examples of such epoxy compounds are all those described in Handbook of Epoxy Resins (Lee et al., McGraw Hill Book Co. 1967) and include glycidyl ethers, thioethers, amines, polyamines and esters.

In a preferred mode of the process, the epoxy compounds and carbon dioxide are reacted at 60° C. t 200° C., preferably 60° C. to 160° C., and normal pressure in the presence of the catalyst and the optional presence of dimethylsulfoxide or toluene or monomethyl ether of diethyleneglycol. The reaction time will vary depending on the reactivity of the epoxy compound, the reaction temperature, the specific catalyst and the solvent optionally present.

A substantially complete conversion of the epoxy compounds to 2-oxo-1,3-dioxolanes takes place after 5 to 10 hours under the preferred conditions. The residual content of the epoxy groups can be determined by known methods such as titration with perchloric acid. If the reaction product is desired to have a given degree of epoxy groups therein, the reaction can be stopped at any desired time.

The process of the invention has the advantage that the reaction of epoxy compound and carbon dioxide occurs at a substantially faster reaction rate at substantially normal pressure without any co-catalysts. The reaction rate is about 150% faster than prior art processes. Moreover, the quaternary phosphonium catalysts are rather inert to the reaction with carbon dioxide and the catalytic activity remains substantially intact until the end of the reaction. Moreover, no epoxy side reactions such as homopolymerization occur.

A particular advantage of the process is that of good solubility of the colorless catalysts of formula I in the reaction product whereby products of good color quality are obtained even without separation. The purified reaction products of EPA 212,409 prepared with ammonium salt cataysts have color values of only 12 to 15 according to Gardner while the cyclic carbonates of the process of the invention have color values of 2 to 5 without purification. Cyclic carbonates derived from glycidyl amines have greater color values due to the higher color value of the starting epoxy compounds and their low thermal stability.

Another advantage of the process of the invention is the high purity of the reaction products and that only small amounts of catalyst are required. This is of particular importance if the reaction products are to be used in the electrical or electronic fields since they should contain a minimum amount of electrolytes for this use. No adverse effects such as softening or stabilization have been seen due to the presence of the catalyst in the reaction product.

One mode of effecting the process is to place the optionally dissolved epoxy compound into a reaction vehicle equipped with a thermometer, a stirrer and a gas inlet and gas outlet pipe and then the quaternary phosphonium catalyst is added. When the reaction mixture reaches the reaction temperature, the catalyst dissolves and then carbon dioxide gas is introduced as rapidly as possible with vigorous stirring without unconsumed excess gas escaping through the outlet pipe. All of the carbon dioxide is spontaneously converted so that there is no noticable gas pressure build up. The reaction is continued until the desired residual epoxy content determined by titration is reached and then the optionally present solvent may be distilled off at reduced pressure.

In the following examples, there are described several preferred embodiments to illustrate the invention. However, it is to be understood that the invention is not intended to be limited to the specific embodiments.

EXAMPLE 1

Into a reaction vessel equipped with thermometer, stirrer and gas inlet and outlet pipe, 186 g of epoxy resin VE 0162 were placed and mixed with 2.1 g of ethyltriphenyl phosphonium bromide. The mixture was heated with stirring to a temperature of 140° C. whereby the catalyst dissolved. The stirring speed was increased and carbon dioxide was introduced in the form of fine gas bubbles so that the introduced gas was completely consumed by the reaction. The course of the reaction was monitored by repeatedly taking samples and determining the residual content of epoxy groups by titration with perchloric acid by the process described in DIN 16,945. In the case of glycidylated amines, the pyridine-hydrochloric acid process was used which is described in Lee, et al Handbook of Epoxy resins, McGraw Hill New York, 1976, pp. 4 to 17.

A pure and therefore high-melting product capable of crystallization (melting temperature = 150° C.) which precipitated as a crystalline solid at the end of the reaction terminating at 140° C. was obtained and to complete the reaction, the temperature was then raised to approximately 160° C. After 9 hours, the content of functional spoxy groups had decreased to 0.6%, and the reaction was terminated. The product exhibited the following properties: melting point: 150° C. and a color value: 2 determined according to Gardner Results of furtehr conversions carried out in the same way are summarized in Table 1. Therein the abreviations indicate:

| | |
|---|---|
| VE 0162 | Bisphenol A-diglycidylether, distilled quality |
| VE 0164 | Bisphenol A-diglycidylether, technical quality |
| VE 0161 | Bisphenol F-diglycidylether |
| VE 0300 | Epoxidized phenol-novolak |
| VE 4162 | Epozidized pentaerythrite |
| VE 3650 | N,N-diglycidylaniline |
| VE 2895 LV | Tetraglycidylmethylene dianiline |
| CY 160 | Hexahydrophthalic acid diglycidyl ester |
| Diluting agent S | Hexanediol diglycidylether |
| Diluting agent T | Trimethylolpropane glycidylether |

COMPARISON EXAMPLE

For comparison, the resin of Example 1, VE 0162, was converted acording to the general rule for the production of bicarbonates from diglycidylethers of bisphenol A from EP-A 212,409 with tetraethylammoniuim bromide as catalyst and KI as co-catalyst (Table 1, No. 13). A cyclic carbonate colored orange and less pure and therefore not capable of crystallization was obtained which upon cooling to room tempeature, solidified, becoming vitreous and having a softening temperature of 51° C. to 52° C.

TABLE 1

| No. | EP resin | EP No. % | Quantity Parts | Catalyst Parts | Catalyst % | Solvent | Solvent Parts | Temp. °C. |
|---|---|---|---|---|---|---|---|---|
| 1 | VE 0162 | 9.3 | 1,860 | 21 | 1.12 | — | — | 140-160 |
| 2 | VE 0164 | 8.6 | 2,670 | 27 | 1.01 | — | — | 140 |
| 3 | VE 0164 | 8.6 | 2,940 | 31 | 1.05 | — | — | 60 |
| 4 | VE 0164 | 8.6 | 3,060 | 32 | 1.05 | — | — | 200 |
| 5 | VE 0161 | 9.2 | 2,810 | 30 | 1.07 | — | — | 140 |
| 6 | VE 0300 | 9.1 | 2,950 | 30 | 1.02 | — | — | 160 |
| 7 | Dil. agent S | 11.2 | 1,500 | 16 | 1.06 | — | — | 100 |
| 8 | Dil. agent T | 10.9 | 2,830 | 29 | 1.02 | — | — | 100 |
| 9 | VE 4162 | 9.9 | 2,814 | 30 | 1.07 | — | — | 120 |
| 10 | CY 160 | 9.5 | 3,096 | 31 | 1.02 | — | — | 120 |
| 11 | VE 2895 LV | 13.8 | 2,800 | 29 | 1.03 | toluene | 2,000 | 100 |
| 12 | VE 3650 | 13.7 | 2,000 | 21 | 1.05 | — | — | 100-120 |
| 13 | Comparison Experiment VE 0162 | 9.3 | 1,860 | 21 | 1.12 + 20 parts co-catalyst KJ (1.1%) | — | — | 140 |
| 14 | VE 0164 | 8.6 | 2,961 | 2.7 | 0.09 | — | — | 140 |
| 15 | VE 0164 | 8.6 | 3,049 | 98 | 3.21 | — | — | 140 |

| No. | Reaction Time hrs. | Yield Parts | Yield % | Residual EP content % | Melting Point °C. | Color value EP resin | Color value Cycl. Carb. |
|---|---|---|---|---|---|---|---|
| 1 | 9 | 2.234 | 95.6 | 0.2 | 150 | 1 | 2 |
| 2 | 6.5 | 3.206 | 97.2 | 0.1 | 49 | 2 | 2 |
| 3 | 18 | 3.210 | *) | 2.2 | (highly viscous) | 2 | 2 |
| 4 | 7 | 3.502 | *) | 1.5 | (nearly solid) | 2 | 12 |
| 5 | 8.5 | 3.415 | 96.8 | 0.2 | 41 | 4 | 5 |
| 6 | 14 | 3.460 | 94.1 | 0.2 | 76 | 5 | 5 |
| 7 | 10 | 1.911 | 97.3 | 0.2 | (liquid) | 1 | 2 |
| 8 | 10 | 3.516 | 95.5 | 0.2 | (liquid) | 1 | 2 |
| 9 | 8 | 3.501 | 97.9 | 0.2 | (highly viscous) | 2 | 3 |
| 10 | 5 | 3.780 | 96.8 | 0.1 | (nearly solid) | 2 | 4 |
| 11 | 10 | 3.692 | 95.5 | 0.4 | 74 | 10 | 17 |
| 12 | 9 | 2.612 | 94.7 | 0.3 | (nearly solid) | 4 | 14 |
| 13 | Comparison Experim. 19 | 2.238 | 95.7 | 0.2 | 51-52 | 1 | 13-14 |
| 14 | 15 | 3.549 | 97.9 | 0.3 | 48 | 2 | 3 |
| 15 | 3.5 | 3.670 | 97.4 | 0.1 | 50-51 | 2 | 3 |

*) Partial conversion of EP groups

Various modifications of the catalysts and process of the invention may be made without departing from the spirit or scope thereof and it is to b understood that the invention is intended to be limited only as defined in the appended claims.

We claim:

1. A process for the preparation of 2-oxo-1,3-dioxolanes consisting essentially of reacting an epoxy compound having at least one epoxy group in the optional presence of an inert solvent with carbon dioxide at 60° C. to 200° C. at normal pressure in the presence of a quaternary phosphonium halide as sole catalyst of the formula $(R_1R_2R_3R_4)P^+X^-$ wherein $R_1$, $R_2$, $R_3$ and $R_4$ are individually selected from the group consisting of phenyl and benzyl optionally substituted with alkyl of 1 to 4 carbon atoms and alkyl of 1 to 4 carbon atoms and $X^-$ is epoxy compound.

2. The process of claim 1 wherein the amount of catalyst is 0.05 to 10% weight based on the amount of epoxy compound.

3. The process of claim 1 wherein the amount of catalyst is 0.1 to 5% by weight based on the amount of epoxy compound.

4. The process of claim 1 wherein the epoxy compound has at least one terminal epoxy group.

5. The process of claim 1 wherein the epoxy compound is selected from the group consisting of a glycidyl ether, a glycidylated amine, a glycidylated polyamine and a glycidyl ester.

6. The process of claim 1 wherein not all the epoxy groups are reacted.

7. A process for the preparation of 2-oxo-1,3-dioxolanes consisting essentially of reacting an epoxy compound having at least one epoxy group with carbon dioxide in the optional presence of an inert solvent and in the presence of a quaternary phosphonium halide catalyst selected from the group consisting of ethyltriphenyl phosphonium bromide, tetrabutyl phosphonium bromide, tetraphenyl phosphonium chloride,, butyltriphenyl phosphonium chloride, 4-ethoxybenzyltriphenyl phosphonium bromide and methoxymethyltrithenyl phosphonium chloride.

* * * * *